(12) United States Patent
Ergler et al.

(10) Patent No.: US 9,750,467 B2
(45) Date of Patent: Sep. 5, 2017

(54) DIRECT CONVERSION X-RAY DETECTOR, CT SYSTEM, AND ASSOCIATED PROCEDURE

(71) Applicant: Siemens Aktiengesellschaft, München (DE)

(72) Inventors: Thorsten Ergler, Erlangen (DE); Edgar Göderer, Forchheim (DE); Björn Kreisler, Hausen (DE); Mario Reinwand, Breitbrunn (DE); Christian Schröter, Bamberg (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 212 days.

(21) Appl. No.: 14/609,621

(22) Filed: Jan. 30, 2015

(65) Prior Publication Data

US 2015/0216485 A1 Aug. 6, 2015

(30) Foreign Application Priority Data

Jan. 31, 2014 (DE) .................. 10 2014 201 772

(51) Int. Cl.
*G01N 23/00* (2006.01)
*A61B 6/03* (2006.01)
(Continued)

(52) U.S. Cl.
CPC ............ *A61B 6/032* (2013.01); *A61B 6/4233* (2013.01); *A61B 6/4291* (2013.01); *G01T 1/241* (2013.01); *G01T 1/2928* (2013.01)

(58) Field of Classification Search
None
See application file for complete search history.

(56) References Cited

U.S. PATENT DOCUMENTS

| 1,331,018 A | * | 2/1920 | Luthy | ...................... H01M 2/18 429/143 |
| 3,824,680 A | * | 7/1974 | Kozlov | .................. H01L 31/00 29/592.1 |

(Continued)

FOREIGN PATENT DOCUMENTS

| CN | 101207141 A | 6/2008 |
| CN | 102066976 A | 5/2011 |

(Continued)

OTHER PUBLICATIONS

Chinese Office Action and English translation thereof dated Jan. 25, 2017.

*Primary Examiner* — Andrew Smyth
(74) *Attorney, Agent, or Firm* — Harness, Dickey & Pierce, P.L.C.

(57) ABSTRACT

A direct conversion X-ray detector for the detection of X-rays includes at least a semiconductor used for detecting X-rays, which has areas that are shaded against X-rays and unshaded areas, a pixelated electrode attached to the semiconductor and an all-over electrode attached to the semiconductor opposite the pixelated electrode, and at least one light source to illuminate the all-over electrode with additional light radiation for the purpose of generating additional charge carriers. In an embodiment, the at least one light source is designed such that the shaded areas are irradiated with a different intensity of the additional light radiation than are the unshaded areas. A CT system including the direct conversion X-ray detector is also disclosed, together with a method for the detection of incident X-rays via direct conversion X-ray detector, wherein the shaded areas are irradiated with a different intensity of the additional light radiation than the unshaded areas.

28 Claims, 3 Drawing Sheets

(51) Int. Cl.
*G01T 1/24* (2006.01)
*G01T 1/29* (2006.01)
*A61B 6/00* (2006.01)

(56) References Cited

U.S. PATENT DOCUMENTS

| | | | |
|---|---|---|---|
| 5,396,072 A * | 3/1995 | Schiebel | H01L 27/14659 |
| | | | 250/370.09 |
| 5,821,539 A * | 10/1998 | Matz | G01T 1/241 |
| | | | 250/370.01 |
| 6,218,668 B1 * | 4/2001 | Luke | G01T 1/2928 |
| | | | 250/370.01 |
| 7,705,319 B2 * | 4/2010 | Bale | G01T 1/24 |
| | | | 250/338.4 |
| 7,800,071 B2 * | 9/2010 | Shahar | G01T 1/24 |
| | | | 250/370.01 |
| 2008/0164418 A1 * | 7/2008 | Shahar | G01T 1/24 |
| | | | 250/370.01 |
| 2009/0110144 A1 * | 4/2009 | Takahashi | G01T 1/2928 |
| | | | 378/62 |
| 2010/0078559 A1 * | 4/2010 | Szeles | G01T 1/00 |
| | | | 250/338.4 |
| 2011/0079865 A1 | 4/2011 | Vogtmeier et al. | |
| 2011/0253886 A1 * | 10/2011 | Hackenschmied | G01T 1/249 |
| | | | 250/252.1 |

FOREIGN PATENT DOCUMENTS

| | | | | |
|---|---|---|---|---|
| DE | 102010015422 A1 * | 10/2011 | | G01T 1/249 |
| DE | 102010015422 A1 | 10/2011 | | |
| DE | 102010015422 B4 * | 4/2013 | | G01T 1/249 |
| DE | 10201221341 B3 | 9/2013 | | |
| DE | 102012213410 B3 * | 9/2013 | | H01L 31/0224 |
| DE | 102012213409 B3 * | 11/2014 | | G01T 1/24 |
| DE | 102012213409 B3 | 11/2014 | | |
| IL | WO 2012153210 A2 * | 11/2012 | | G01T 1/244 |
| IL | WO 2012153210 A3 * | 4/2013 | | G01T 1/244 |
| WO | WO-2012153210 A2 | 11/2012 | | |

* cited by examiner

DIRECT CONVERSION X-RAY DETECTOR, CT SYSTEM, AND ASSOCIATED PROCEDURE

PRIORITY STATEMENT

The present application hereby claims priority under 35 U.S.C. §119 to German patent application number DE 102014201772.6 filed Jan. 31, 2014, the entire contents of which are hereby incorporated herein by reference.

FIELD

At least one embodiment of the invention generally relates to a direct conversion X-ray detector for the detection of X-rays, at least having a semiconductor used for detecting X-rays, which has areas that are shaded against X-rays and unshaded areas, a pixelated electrode attached to the semiconductor and an all-over electrode attached to the semiconductor opposite the pixelated electrode, and at least one light source which illuminates the all-over electrode with additional light radiation for the purpose of generating additional charge carriers.

At least one embodiment of the invention further generally relates to a CT system, and/or a method for the detection of incident X-rays by way of a direct conversion X-ray detector.

BACKGROUND

For the detection of gamma- and X-rays, in particular in CT, dual-energy CT, SPECT and PET systems, the facilities used include direct conversion detectors based on semiconducting materials, such as CdTe, CdZnTe, CdZnTeSe, CdTeSe, CdMnTe, InP, TlBr2, HgI2. However, with these materials a polarization effect arises, particularly in the case of the high radiation flux density which is necessary for CT devices.

Polarization is the term used for the reduction in the detected count rate when there are high photon or radiation fluxes, as applicable. This polarization is caused by the very low mobility of the charge-carriers, above all at the sites of electron vacancies, or holes, and by the concentration of intrinsic imperfections in the semiconductor. The polarization thus arises from the reduction in the electric field due to fixed-location charges which are associated with imperfections, the so-called spatial charge of the semiconductor, which act as capture and recombination centers for the charge carriers produced by the X-rays. This reduces the life and mobility of the charge carriers, which in turn leads to a reduction in the detected count rate at the high radiation flux densities.

The spatial charge in the semiconductor can be unevenly distributed in the material, due to inhomogenity of the X-rays incident on the semiconductor, and can change over the course of the irradiation. A consequence of these changes is a lateral displacement of the counted events which are detected in the pixelated electrode. That is to say, the count rate of neighboring pixels are different, causing the spatial assignment of the counted events to be incorrect. Ultimately, the result is image artifacts.

Usually, the inhomogeneities in the irradiation of the semiconductor are caused by the object under investigation. In particular, the X-rays have different directions of incidence for the individual beams, due to their different scattering in the object under investigation. Consequently it is not possible to predict exactly the direction from which the X-rays strike the semiconductor. Typically however, use is made of scattered radiation grids, which absorb the X-rays which have been scattered through the object under investigation, and thereby homogenize the X-rays incident on the semiconductor. Here, the position of the scattered radiation grid is fixed relative to the semiconductor, so that the spatial inhomogeneity in the X-rays caused by the scattered radiation grid, and hence also the spatial charge, is known, because no radiation strikes in the areas directly beneath the scattered radiation grid.

Further inhomogeneities in the spatial charge can be caused by the metalized pixelated electrode attached onto the semiconductor. In the non-metalized areas of the semiconductor, that is the areas of the semiconductor which are not covered by a pixel, the electric field is weaker, and under X-ray irradiation a higher spatial charge forms.

Further inhomogeneities in the spatial charge are caused by imperfections in the material which are, however, unevenly distributed. Since their occurrence in the semiconductor cannot be controlled in terms of their spatial arrangement and frequency, it would be necessary to measure separately in each individual detector the effects they cause, in order to take these inhomogeneities into account.

Until now there has been no known solution as to how to compensate the entire inhomogeneity in the spatial charge in the semiconductor.

SUMMARY

At least one embodiment of the invention is directed to a direct conversion X-ray detector in which an inhomogeneous formation of the spatial charge in the semiconductor is prevented or compensated for. At least one embodiment of the invention is directed to a CT system with a direct conversion X-ray detector together with an associated procedure.

Advantageous developments of the invention are the subject of the subordinate claims.

Accordingly, in at least one embodiment the inventors propose to improve a direct conversion X-ray detector for the detection of X-rays, in particular for use in a CT system, at least having a semiconductor used for the purpose of detecting X-rays, which has areas which are shaded from X-rays and unshaded areas, a pixelated electrode attached onto the semiconductor and an all-over electrode attached onto the semiconductor opposite the pixelated electrode, and at least one light source which illuminates the all-over electrode with additional light radiation for the purpose of generating additional charge carriers, to the effect that the at least one light source is designed in such a way that the shaded areas are irradiated with a different intensity of the additional light radiation than are the unshaded areas. By illuminating the semiconductor with different intensities, it is possible to compensate for the inhomogeneously formed spatial charge.

Also falling within the ambit of at least one embodiment of the invention is a CT system having a direct conversion X-ray detector as described above, with which computer-tomographic recordings of an object under investigation can be produced. A CT system with the inventive X-ray detector advantageously guarantees drift-free measurement of the absorption of the radiation, so that the recordings produced are advantageously free of image artifacts.

It is further proposed, in at least one embodiment, to improve a method for the detection of incident X-rays by way of a direct conversion X-ray detector, in particular for use in a CT system, at least with a pixelated electrode attached onto a semiconductor and an all-over electrode attached onto the semiconductor opposite the pixelated electrode, wherein the semiconductor has areas which are shaded from X-rays and unshaded areas, and at least one light source which illuminates the all-over electrode with additional light radiation for the purpose of generating additional charge carriers, in that the shaded areas are irradiated with a different intensity of the additional light radiation than the unshaded areas.

BRIEF DESCRIPTION OF THE DRAWINGS

The invention is described in more detail below by reference to the preferred example embodiments with the help of the figures, in which only the features necessary for an understanding of the invention are shown. The following reference marks are used: 1: semiconductor; 2: subpixel; 3: image pixel; 4: cathode; 5: grid strip; 6: overprint; C1: CT system; C2: first X-ray tube; C3: first detector; C4: second X-ray tube (optional); C5: second detector (optional); C6: gantry housing; C7: patient; C8: patient table; C9: system axis; C10: computation and control unit; Prg1 to Prgn: computer programs.

Specifically shown are.

DETAILED DESCRIPTION OF THE EXAMPLE EMBODIMENTS

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

Before discussing example embodiments in more detail, it is noted that some example embodiments are described as processes or methods depicted as flowcharts. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Methods discussed below, some of which are illustrated by the flow charts, may be implemented by hardware, software, firmware, middleware, microcode, hardware description languages, or any combination thereof. When implemented in software, firmware, middleware or microcode, the program code or code segments to perform the necessary tasks will be stored in a machine or computer readable medium such as a storage medium or non-transitory computer readable medium. A processor(s) will perform the necessary tasks.

Specific structural and functional details disclosed herein are merely representative for purposes of describing example embodiments of the present invention. This invention may, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

In the following description, illustrative embodiments may be described with reference to acts and symbolic representations of operations (e.g., in the form of flowcharts) that may be implemented as program modules or functional processes include routines, programs, objects, components, data structures, etc., that perform particular tasks or implement particular abstract data types and may be implemented using existing hardware at existing network elements. Such existing hardware may include one or more Central Processing Units (CPUs), digital signal processors (DSPs), application-specific-integrated-circuits, field programmable gate arrays (FPGAs) computers or the like.

Note also that the software implemented aspects of the example embodiments may be typically encoded on some form of program storage medium or implemented over some type of transmission medium. The program storage medium (e.g., non-transitory storage medium) may be magnetic (e.g., a floppy disk or a hard drive) or optical (e.g., a compact disk read only memory, or "CD ROM"), and may be read only or random access. Similarly, the transmission medium may be twisted wire pairs, coaxial cable, optical fiber, or some other suitable transmission medium known to the art. The example embodiments not limited by these aspects of any given implementation.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

The inventors have recognized that it is possible to compensate for the inhomogeneously formed or distributed spatial charge, occurring in a semiconductor used for the detection of X-rays, in order furthermore to avoid the polarization of the detector, caused by the spatial charges, together with the artifacts in the imaging which follow from it. In particular, it is possible to compensate the spatial charges occurring due to inhomogeneous X-ray irradiation, due to an inhomogeneous electric field and due to the uncontrolled occurrence of impurities in the semiconductor.

For the purpose of balancing out the spatial charges, an all-over or continuous electrode, which is attached to the semiconductor, is illuminated by additional light radiation. A suitable wavelength for the light radiation is in the visible or infrared region. Particular areas of the electrode are illuminated with different intensities. In doing so account is taken of the inhomogeneities in the X-rays, caused by the scattered radiation grid, and the metallization structure of the semiconductor, that is the arrangement and formation of the individual pixels of the pixelated electrode on the semiconductor, together with the shading of certain areas of the semiconductor from the X-rays, in order selectively to compensate the spatial charge.

There are several variants of how to achieve different intensities of illumination. Basically, it is possible either to shade a uniform illuminating light to different extents, so that between the shaded and unshaded areas there is a difference in the intensity of the illumination. Or a non-uniform light beam can be applied, this having appropriately different intensities.

In one variant, use can be made of a homogeneous uniform light beam, which is shaded to different extents in certain areas in order thereby to illuminate particular areas of the semiconductor and the electrode with different intensities. The homogeneous illumination can be achieved, in particular, by a reflective layer on the side of the scattered radiation grid which faces towards the semiconductor. To effect the shading, a coating which is at least partially light-transmitting is suitable. For example, a coating on the electrode in the form of an overprint can be used. In particular, in the shading of the light radiation account can be taken of the shading of the X-rays by the scattered radiation grid or of the structure of the pixelated electrode. For example, areas of the semiconductor which are screened off or shaded from the X-rays by the scattered radiation grid are illuminated with a greater intensity than other areas, which are not screened off or shaded, or vice versa. In this case, the geometry of the shading is adapted to the geometry of the scattered radiation grid. Equally, the shading can be adapted both to the arrangement of the scattered radiation grid and also to the metallization structure of the electrode, or different gray values are used for the overprint, in order to achieve a selective weakening of the illumination.

The electrode can have an electrical connection to a voltage source. This electric connection is preferably of transparent construction.

By way of the partial shading or weakening of the additional illumination of the detector, it is possible to compensate for the predictable inhomogeneities in the spatial charge in the semiconductor. Thus it is possible, for example, to illuminate more strongly areas which are more weakly exposed to the X-rays, such as under the scattered radiation grid, so as to achieve greater overall homogeneity in the total radiation, that is the sum of the X-rays and the illumination by the light radiation. Equally, it is possible, for example, to illuminate more weakly the low-field non-metalized areas, in order to reduce the charging in these volumes within the semiconductor. Depending on the sign of the spatial charge and of the charge carriers generated by the illumination, the modulation of the additional illumination can also be oppositely applied.

Overall, the additional illumination leads to more limited displacement of the detected count results, and thus to fewer image artifacts.

Accordingly, in at least one embodiment the inventors propose to improve a direct conversion X-ray detector for the detection of X-rays, in particular for use in a CT system, at least having a semiconductor used for the purpose of detecting X-rays, which has areas which are shaded from X-rays and unshaded areas, a pixelated electrode attached onto the semiconductor and an all-over electrode attached onto the semiconductor opposite the pixelated electrode, and at least one light source which illuminates the all-over electrode with additional light radiation for the purpose of generating additional charge carriers, to the effect that the at least one light source is designed in such a way that the shaded areas are irradiated with a different intensity of the additional light radiation than are the unshaded areas. By illuminating the semiconductor with different intensities, it is possible to compensate for the inhomogeneously formed spatial charge.

In this situation, in one form of embodiment, the irradiation of the individual areas with the additional light radiation, that is of the shaded areas and the unshaded areas, is in each case homogeneous. In contrast to this, in another form of embodiment the irradiation of the individual areas with the additional light radiation is in each case inhomogeneous. Using respectively the homogeneity or inhomogeneity of the light radiation, known in each case, it is possible to determine more precisely the compensation for the inhomogeneities in the spatial charge in the semiconductor.

The X-ray detector has a semiconductor on which is attached, on each of two opposite sides, an electrode to which it has an electrically conducting connection. In accordance with at least one embodiment of the invention, one electrode is in the form of a pixelated electrode and the other electrode is in the form of an all-over electrode. The pixelated electrode is preferably arranged on the side of the semiconductor which faces away from the X-rays, and the all-over electrode correspondingly on the opposite side facing the X-rays. Depending on the polarity of the X-ray radiation detector, the pixelated electrode forms the anode and the all-over electrode the cathode, or vice versa.

The X-ray detector can have a scattered radiation grid for the purpose of reducing the incidence of scattered X-rays on the semiconductor, so that the shading of the semiconductor against the X-rays is effected by the scattered radiation grid. The intensity of the illumination is then preferably adapted to the scattered radiation grid. The shaded areas are almost completely screened off from the incident X-rays by the strips of the grid, that is to say they are only minimally irradiated, or not at all, as applicable. Correspondingly, in these areas the spatial charge is lower than in the areas which are not screened off by the grid strips. Hence, in one preferred form of embodiment, for the purpose of balancing out the spatial charge the intensity of the light radiation applied to the shaded areas is greater than the intensity of the light radiation applied to the unshaded areas. In this way, by means of a balancing out of the total radiation incident on the semiconductor, a balancing out of the spatial charge is achieved.

An alternative form of embodiment provides for the opposite, that the intensity of the light radiation applied to the shaded areas is less than the intensity of the light radiation applied to the unshaded areas. For example, for this purpose there can be, attached to the underside of the grid strips, that is on the ends of the grid strips which face towards the electrode, a reflective layer which additionally reflects the light radiation onto the shaded areas.

Another possibility for balancing out the spatial charges consists in illuminating the semiconductor, and correspondingly also the electrode arranged on the semiconductor, with a uniform light radiation, but with this being shaded to different extents. In consequence, the shading of the unshaded areas and the shaded areas from the light radiation is also different. In one preferred form of embodiment, the shading of the unshaded areas is greater than the shading of the shaded areas. Hence, the shaded areas are illuminated with a greater intensity than the unshaded areas. However, another form of embodiment provides the reverse, that the shading of the unshaded areas is less than the shading of the shaded areas.

For the purpose of shading off the pixelated electrode or to attenuate the light radiation, as applicable, in one preferred form of embodiment the all-over electrode attached onto the semiconductor opposite the pixelated electrode is constructed with differing transparency. Advantageously, the all-over electrode is at least partially semi-transparent. For example, an arrangement of areas of the all-over electrode with differing transparencies is adapted to the geometry of the scattered radiation grid.

The transparency of the all-over electrode can, for example, be reduced by an overprint. Correspondingly, in an advantageous form of embodiment the all-over electrode has, at least partially, an overprint. This overprint is with further advantage at least partially impenetrable to light, in order to attenuate the light radiation applied to the pixelated electrode. For the overprint, a material which is at least partially impenetrable to light is suitable, such as for example a printed-on foil. Equally, the transparency of the overprint, that is the strength of the shading, can be influenced by different gray values in the overprint. The overprint can be implemented between completely transparent and black.

The pixelated electrode is arranged on the semiconductor, in one preferred form of embodiment on the side of the semiconductor facing towards the X-rays. In accordance with the invention, the at least one light source illuminates the semiconductor through the pixelated electrode. In this case the pixelated electrode can be illuminated either directly or indirectly, that is to say through the all-over electrode and the semiconductor. Correspondingly, the at least one light source is arranged either on the side of the semiconductor facing towards the X-rays or on the side of the semiconductor facing away from the X-rays. Indirect illumination of the pixelated electrode, that is from the direction of the all-over electrode, is suitable above all for reducing the intensity by shading of the semiconductor by means of an all-over electrode with differing transparency. In one form of embodiment of the X-ray detector, precisely one light source is provided. Other forms of embodiment provide more than one light source, for example two, three or four light sources. Multiple light sources could, for example, be arranged on different sides of the semiconductor or the electrodes, as applicable.

One form of embodiment of the X-ray detector provides that the pixelated electrode has a plurality of sub-pixels, wherein a group of subpixels is in each case linked to a counting pixel used for the purpose of detection, and further non-counting subpixels which are not used for detection are electrically connected to each other. The image pixels are thus used for the purpose of detecting the incident X-rays, and so are counting image pixels. The remaining subpixels are not used for detection, and are therefore referred to as non-counting. For example, 4, 9, 16 etc. subpixels could in each case be combined to form a square image pixel. Arranged between the subpixels there is preferably in each case a row of subpixels.

Advantageously, the counting image pixels are arranged in the unshaded areas of the pixelated electrode. Correspondingly, the non-counting pixels are advantageously arranged in the shaded areas. In one form of embodiment of the X-ray detector with a scattered radiation grid, the non-counting pixels are arranged beneath the grid strips of the scattered radiation grid, that is, looking in the direction of incidence of the X-ray radiation. The counting image pixels are correspondingly advantageously arranged in the open, that is unshaded, areas beneath the grid strips. The shaded pixels are almost completely screened by the grid strips from the incident X-rays, that is to say they are irradiated only minimally or not at all, as applicable. One form of embodiment provides that the shading of the counting image pixels is greater than the shading of the non-counting subpixels.

For the additional light radiation, light with a wavelength in the infrared and/or the visible region is to be preferred above all.

Also falling within the ambit of at least one embodiment of the invention is a CT system having a direct conversion X-ray detector as described above, with which computer-tomographic recordings of an object under investigation can be produced. A CT system with the inventive X-ray detector advantageously guarantees drift-free measurement of the absorption of the radiation, so that the recordings produced are advantageously free of image artifacts.

It is further proposed, in at least one embodiment, to improve a method for the detection of incident X-rays by way of a direct conversion X-ray detector, in particular for use in a CT system, at least with a pixelated electrode attached onto a semiconductor and an all-over electrode attached onto the semiconductor opposite the pixelated electrode, wherein the semiconductor has areas which are shaded from X-rays and unshaded areas, and at least one light source which illuminates the all-over electrode with additional light radiation for the purpose of generating additional charge carriers, in that the shaded areas are irradiated with a different intensity of the additional light radiation than the unshaded areas.

The light radiation can be applied either directly onto the semiconductor or indirectly, in that the illumination is either onto the pixelated electrode, or is on the all-over electrode side and the pixelated electrode is then illuminated through the semiconductor. The different intensities are advantageously achieved by different illumination or a difference in the shading of the pixelated electrode. Here, the irradiation of the shaded areas and the irradiation of the unshaded areas are each either homogeneous or inhomogeneous.

Figure 1:
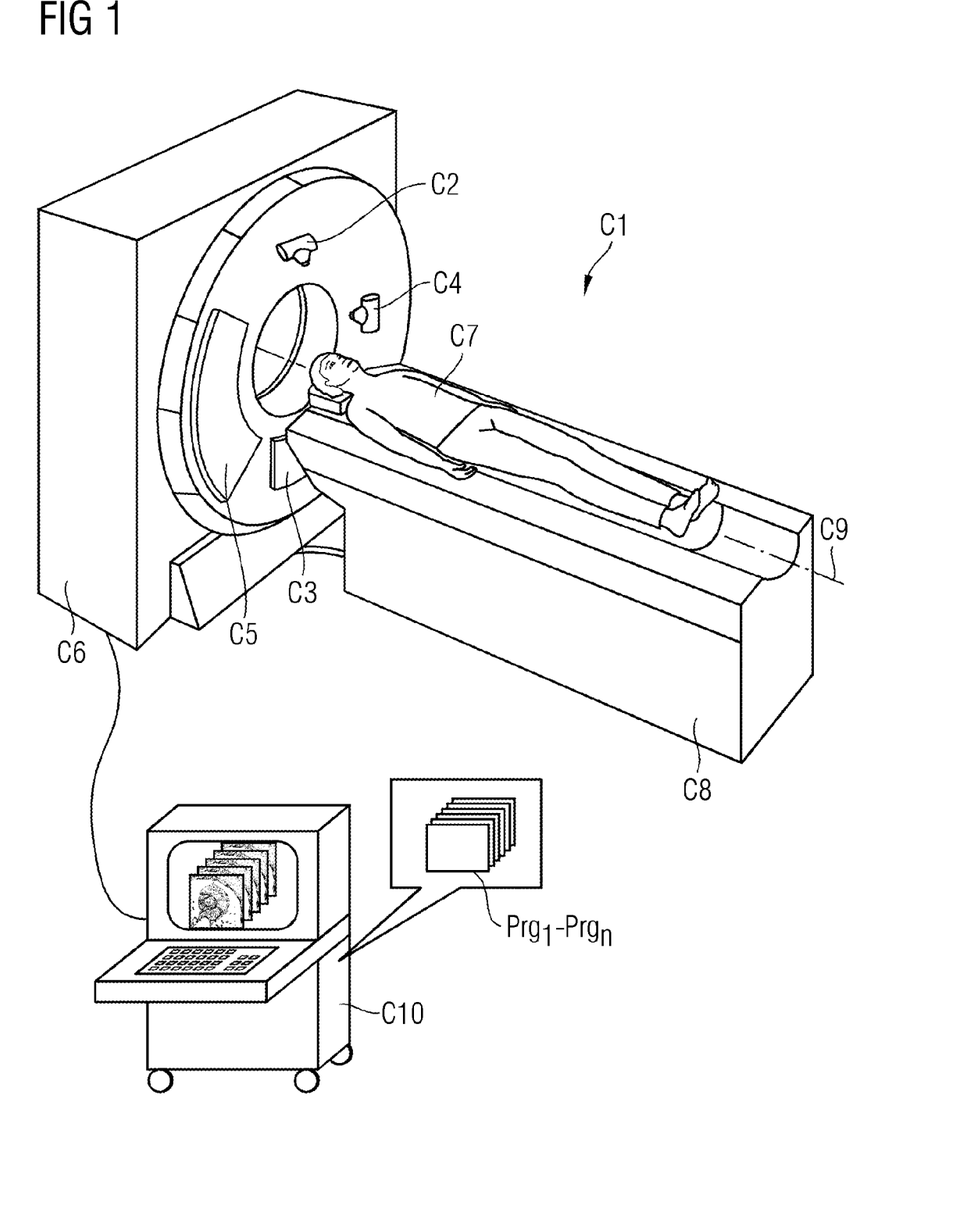
FIG. 1 a schematic diagram of a CT system with computational unit.

FIG. 1 shows an example of a CT system C1. The CT system C1 incorporates a gantry housing C6 in which there is a gantry, not shown in more detail here, on which is affixed a first X-ray tube C2, with a first detector C3 opposite it. Optionally, a second X-ray tube C4 is provided, with a second detector C5 opposite it. There is a patient C7 on a patient table C8 which can be moved in the direction of the system axis C9 and with which, during the scanning using X-rays, he can be moved, either continually or in steps, along the system axis C9 through a measurement field between the X-ray tubes C2 and C4 and their respective associated detectors C3 and C5. This procedure is controlled by a computing and control unit C10 with the help of computer programs Prg1 to Prgn.

Figure 2:
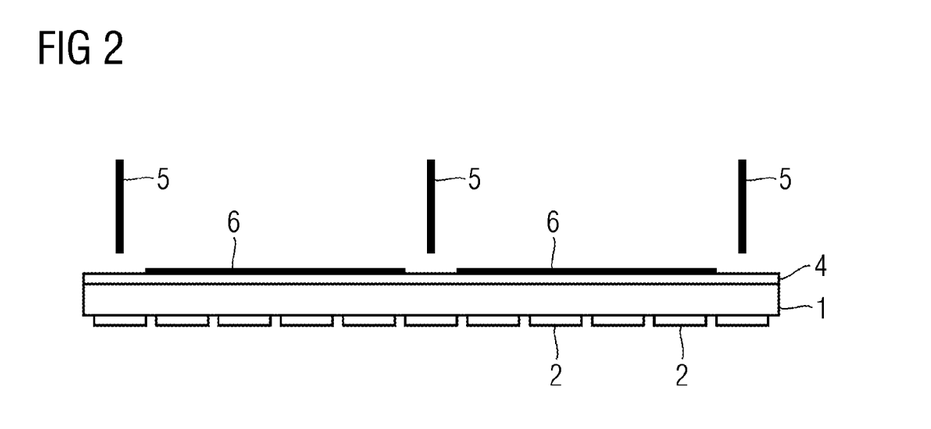
FIG. 2 a schematic cross-sectional diagram of a section of the X-ray detector, FIG. 3 a schematic plan view of a section of an X-ray detector with differently illuminated electrodes, in a first form of embodiment.
Figure 3:
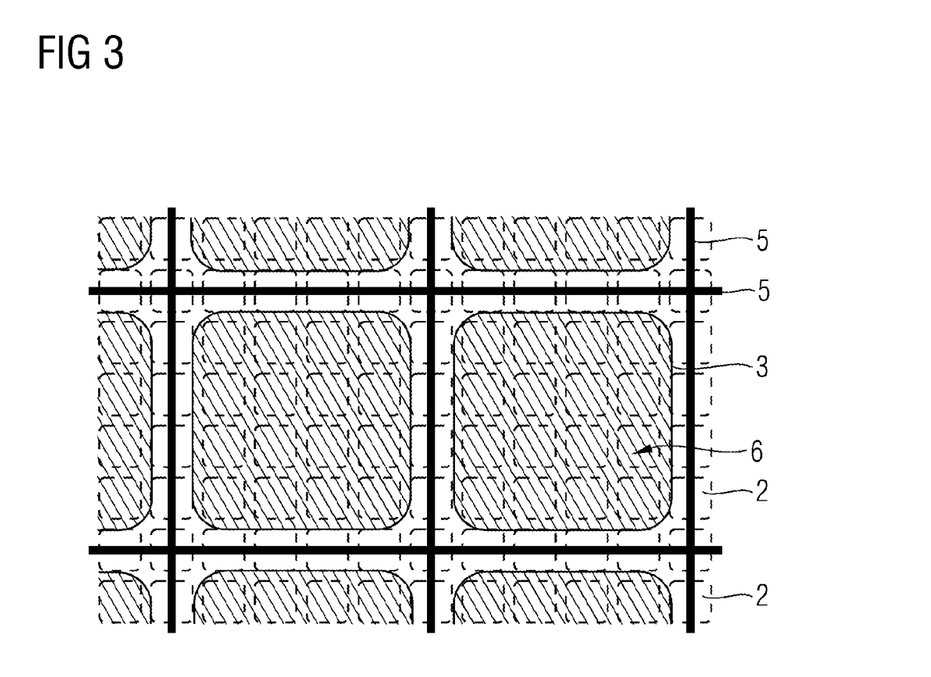

In accordance with an embodiment of the invention, the detectors C3 and C5 are constructed as direct conversion X-ray detectors, which in the form of embodiment shown here have at least one semiconductor for the purposes of detecting X-rays and a pixelated electrode attached to the semiconductor, wherein the semiconductor is illuminated with additional light radiation with different intensities for the purpose of generating additional charge carriers (see FIGS. 2 and 3). The CT system C1 is correspondingly operated in accordance with an embodiment of the inventive procedure.

FIG. 2 shows a schematic cross-sectional diagram of a section of the direct conversion X-ray detector. The detector has a semiconductor 1 used for the purpose of detecting the X-rays. In addition the detector has a pixelated anode attached on the semiconductor, in the form of embodiment shown here on its underside, that is on the side facing away from the X-rays. The anode is subdivided into a plurality of subpixels 2. In each case, 16 adjacently arranged subpixels 2 are here combined for the purpose of detection to form one square counting image pixel, see FIGS. 3 and 4. Arranged between the image pixels there is in each case a row of subpixels 2. These subpixels 2 are not used for detection, that is they are non-counting. The non-counting subpixels 2 have an electrically conducting link to each other.

The detector has in addition a scattered radiation grid. Each of the non-counting subpixels 2 is arranged in the shaded areas of the semiconductor 1 underneath the grid strips 5 of the scattered radiation grid, see also FIGS. 2 and 3. The grid strips 5 thus prevent the incidence of X-rays onto these subpixels 2. The counting image pixels 3 are arranged in the unshaded areas of the semiconductor 1, between the grid strips 5.

Attached to the opposite side of the semiconductor 1 is an all-over cathode 4. The cathode 4 is constructed with differing transparency. In the form of embodiment shown here, the cathode 4 is less light transmissive in the open areas between the grid strips 5, which are thus not screened from the X-rays, than in remaining areas which are screened off by the grid strips 5, so that the image pixels 3 of the pixelated anode are screened against additional illumination by the light radiation. To this end, the cathode 4 has, in the less light transmissive areas, an overprint 6. The overprint is formed of a material which is impenetrable to light.

In addition, the detector also has a further light source, which, for the sake of clarity, is not shown here however. The light source illuminates the pixelated electrode and thus causes additional charge carriers to be produced in the semiconductor, so that an inhomogeneous spatial charge in the semiconductor 1 is balanced out. In accordance with the invention, the illumination differs, so that counting image pixels and non-counting pixels 2 are illuminated with different intensities, see FIGS. 3 and 4.

Figure 4:
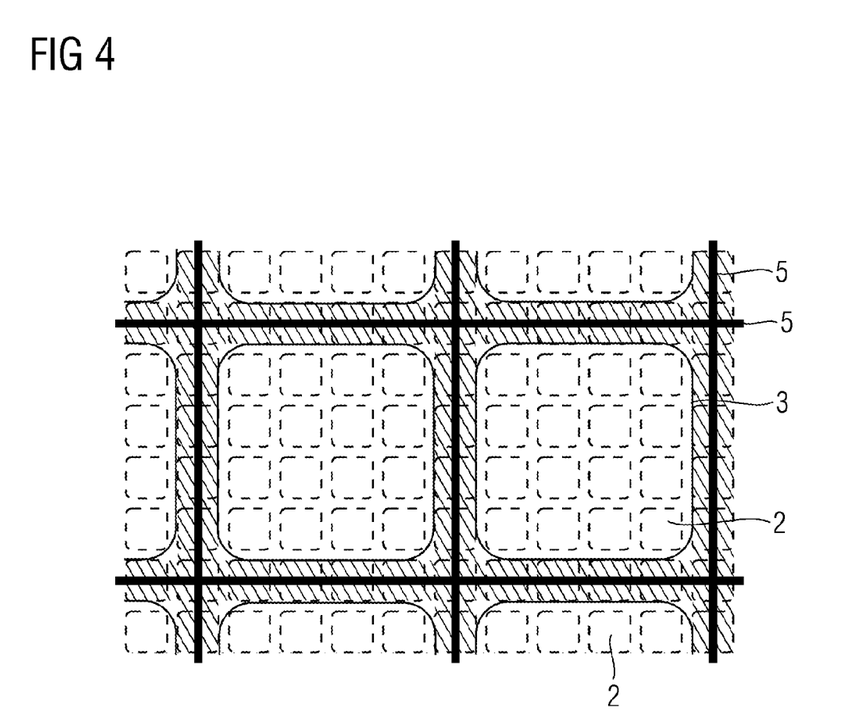
FIG. 4 a schematic plan view of a section of the X-ray detector with differently illuminated electrodes, in another form of embodiment.

FIGS. 3 and 4 each show a schematic plan view of a section of an X-ray detector with differently illuminated pixelated electrodes. The structure of the detector corresponds basically to that of the detector shown in FIG. 2. Components which are the same are identified by the same reference marks. For this reason, there is no further description of components which have already been described.

In FIG. 3, in the shaded areas beneath the grid strips 5, that is in the case of the non-counting subpixels 2, the intensity of the illumination is greater than the intensity of the illumination of the counting image pixels 3 in the unshaded areas. This is achieved in that the light source illuminates the all-over cathode on the upper side of the semiconductor, and the overprint 6 which is impenetrable to light shades the image pixels 3 arranged beneath it. Thus only the non-counting subpixels 2 beneath the grid strips 5 are additionally illuminated. Hence, by differing shading of a uniform illumination the effect is achieved that certain areas of the anode are illuminated with different intensities. The areas which are shaded off, underneath the overprint 6, correspond to the image pixels 3 and are shown hatched. The structure of this form of embodiment corresponds to the detector shown in FIG. 2.

In FIG. 4, the illumination situation shown is precisely the reverse. Here, the unshaded counting image pixels 3 are illuminated more strongly, that is with greater intensity, than the shaded non-counting subpixels 2. To this end, the additional light radiation is applied to the detector from the upper side, and is partially shaded off by the grid strips 5 of the scattered radiation grid, so that the areas between the grid strips 5 are illuminated with greater intensity. The areas beneath the grid strips 5 which are shaded off are shown hatched.

In summary, an embodiment of the invention proposes a direct conversion X-ray detector for the detection of X-rays, at least having a semiconductor used for detecting the X-rays, which has areas that are shaded against X-rays and unshaded areas, a pixelated electrode attached to the semiconductor and an all-over electrode attached to the semiconductor opposite the pixelated electrode, and at least one light source which illuminates with additional light radiation the all-over electrode for the purpose of generating additional charge carriers, wherein the at least one light source is constructed in such a way that the shaded areas are irradiated with a different intensity of the additional light radiation than the unshaded areas.

Further proposed in an embodiment is a CT system having a direct conversion X-ray detector in accordance with the invention, together with a method for the detection of incident X-rays by means of a direct conversion X-ray detector in accordance with the invention, wherein the shaded areas are irradiated with a different intensity of the additional light radiation than the unshaded areas.

Although the invention has been illustrated and described more in detail by the preferred example embodiment, the invention is not restricted to the disclosed examples and other variations could be deduced from it by the person skilled in the art without going outside the scope of protection for the invention.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, tangible computer readable medium and tangible computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a tangible computer readable medium and is adapted to perform any one of the aforementioned methods when run on a computer device (a device including a processor). Thus, the tangible storage medium or tangible computer readable medium, is adapted to store information and is adapted to interact with a data processing facility or computer device to execute the program of any of the above mentioned embodiments and/or to perform the method of any of the above mentioned embodiments.

The tangible computer readable medium or tangible storage medium may be a built-in medium installed inside a computer device main body or a removable tangible medium arranged so that it can be separated from the computer device main body. Examples of the built-in tangible medium include, but are not limited to, rewriteable non-volatile memories, such as ROMs and flash memories, and hard disks. Examples of the removable tangible medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A direct conversion X-ray detector for the detection of X-rays, comprising:
   a semiconductor to detect X-rays, the semiconductor including areas that are shaded against X-rays and areas that area unshaded areas;
   a pixelated electrode, attached to the semiconductor and attached to an all-over electrode, the all-over electrode being attached to the semiconductor opposite the pixelated electrode; and
   at least one light source to illuminate the all-over electrode with additional light radiation to generate additional charge carriers, the at least one light source being designed such that the shaded areas are irradiated with a different intensity of the additional light radiation than the unshaded areas, wherein the intensity of the light radiation applied to the shaded areas is relatively greater than the intensity of the light radiation applied to the unshaded areas.

2. The X-ray detector of claim 1, wherein the irradiation with the additional light radiation, of the both the shaded areas and the unshaded areas, is homogeneous.

3. The X-ray detector of claim 1, wherein the irradiation with the additional light radiation, of the both the shaded areas and the unshaded areas, is inhomogeneous.

4. The X-ray detector of claim 1, further comprising:
   a scattered radiation grid, to reduce an incidence of scattered X-rays on the semiconductor, so that the shading of the semiconductor is effected by the scattered radiation grid.

5. The X-ray detector of claim 1, wherein the all-over electrode includes a differing transparency.

6. The X-ray detector of claim 5, wherein the all-over electrode includes at least in parts an overprint.

7. A direct conversion X-ray detector for the detection of X-rays, comprising:
   a semiconductor to detect X-rays, the semiconductor including areas that are shaded against X-rays and areas that area unshaded areas;
   a pixelated electrode, attached to the semiconductor and attached to an all-over electrode, the all-over electrode being attached to the semiconductor opposite the pixelated electrode; and
   at least one light source to illuminate the all-over electrode with additional light radiation to generate additional charge carriers, the at least one light source being designed such that the shaded areas are irradiated with a different intensity of the additional light radiation than the unshaded areas, wherein the pixelated electrode includes a plurality of subpixels, wherein in each case a group of subpixels is linked into a counting unshaded image pixel, used for detection, and other non-counting shaded subpixels which are not used for detection are electrically linked to each other.

8. The X-ray detector of claim 7, wherein the shading of the counting image pixels is relatively greater than the shading of the non-counting subpixels.

9. The X-ray detector of claim 1, wherein the additional light radiation has a wavelength in at least one of the infrared and the visible region.

10. A CT system comprising:
    the direct conversion X-ray detector of claim 1.

11. A method for the detection of incident X-rays via a direct conversion X-ray detector at least including a pixelated electrode attached to a semiconductor and an all-over electrode attached to the semiconductor opposite the pixelated electrode, wherein the semiconductor includes areas which are shaded against the X-rays and areas which are unshaded, the method comprising:
    irradiating, via at least one light source, the all-over electrode with additional light radiation to generate additional charge carriers, the shaded areas being irradiated with a different intensity of the additional light radiation than the unshaded areas, wherein the intensity of the light radiation irradiated to the shaded areas is relatively greater than the intensity of the light radiation applied to the unshaded areas.

12. The X-ray detector of claim 1, wherein the direct conversion X-ray detector is for use in a CT system.

13. The X-ray detector of claim 7, wherein the intensity of the light radiation applied to the shaded areas is relatively greater than the intensity of the light radiation applied to the unshaded areas.

14. The X-ray detector of claim 7, wherein the intensity of the light radiation applied to the shaded areas is relatively less than the intensity of the light radiation applied to the unshaded areas.

15. The X-ray detector of claim 5, wherein the all-over electrode is at least partially semi-transparent.

16. The X-ray detector of claim 6, wherein the all-over electrode includes at least in parts an overprint which is at least partially impenetrable to light.

17. The X-ray detector of claim 15, wherein the all-over electrode includes at least in parts an overprint which is at least partially impenetrable to light.

18. The X-ray detector of claim 4, wherein the pixelated electrode includes a plurality of subpixels, wherein in each case a group of subpixels is linked into a counting unshaded image pixel, used for detection, and other non-counting shaded subpixels which are not used for detection are electrically linked to each other.

19. The X-ray detector of claim 18, wherein the shading of the counting image pixels is relatively greater than the shading of the non-counting subpixels.

20. The X-ray detector of claim 4, wherein the additional light radiation has a wavelength in at least one of the infrared and the visible region.

21. The method of claim 11, wherein the direct conversion X-ray detector is for use in a CT system.

22. The method of claim 11, wherein the irradiation with the additional light radiation, of the both the shaded areas and the unshaded areas, is homogeneous.

23. The method of claim 11, wherein the irradiation with the additional light radiation, of the both the shaded areas and the unshaded areas, is inhomogeneous.

24. A CT system comprising:
    the direct conversion X-ray detector of claim 7.

25. The X-ray detector of claim 7, wherein the irradiation with the additional light radiation, of the both the shaded areas and the unshaded areas, is homogeneous.

26. The X-ray detector of claim 7, wherein the irradiation with the additional light radiation, of the both the shaded areas and the unshaded areas, is inhomogeneous.

27. The X-ray detector of claim 7, wherein the all-over electrode includes a differing transparency.

28. The X-ray detector of claim 7, wherein the all-over electrode includes at least in parts an overprint which is at least partially impenetrable to light.

* * * * *